United States Patent
Barbee et al.

(10) Patent No.: US 9,267,914 B2
(45) Date of Patent: Feb. 23, 2016

(54) ELECTRIC FIELD DIRECTED LOADING OF MICROWELL ARRAY

(71) Applicant: LIFE TECHNOLOGIES CORPORATION, Carlsbad, CA (US)

(72) Inventors: Kristopher Barbee, East Haven, CT (US); John F. Davidson, Guilford, CT (US); Wolfgang Hinz, Killingworth, CT (US); Shifeng Li, Fremont, CA (US); James Bustillo, Castro Valley, CA (US)

(73) Assignee: Life Technologies Corporation, Carlsbad, CA (US)

( * ) Notice: Subject to any disclaimer, the term of this patent is extended or adjusted under 35 U.S.C. 154(b) by 22 days.

(21) Appl. No.: 14/244,849

(22) Filed: Apr. 3, 2014

(65) Prior Publication Data

US 2014/0217477 A1    Aug. 7, 2014

Related U.S. Application Data

(63) Continuation of application No. PCT/US2012/058599, filed on Oct. 3, 2012.

(60) Provisional application No. 61/542,611, filed on Oct. 3, 2011, provisional application No. 61/550,193, filed on Oct. 21, 2011.

(51) Int. Cl.
*G01N 27/414* (2006.01)
*B01J 19/00* (2006.01)

(52) U.S. Cl.
CPC ......... *G01N 27/4148* (2013.01); *B01J 19/0046* (2013.01); *G01N 27/4145* (2013.01); *B01J 2219/005* (2013.01); *B01J 2219/00286* (2013.01); *B01J 2219/00317* (2013.01); *B01J 2219/00459* (2013.01); *B01J 2219/00466* (2013.01); *B01J 2219/00468* (2013.01); *B01J 2219/00596* (2013.01); *B01J 2219/00648* (2013.01); *B01J 2219/00653* (2013.01);

(Continued)

(58) Field of Classification Search
CPC ............ G01N 27/414; G01N 27/4145; G01N 27/4148

See application file for complete search history.

(56) References Cited

U.S. PATENT DOCUMENTS

| | | | |
|---|---|---|---|
| 2009/0127589 A1 | 5/2009 | Rothberg et al. | |
| 2010/0137143 A1 | 6/2010 | Rothberg et al. | |
| 2010/0300895 A1* | 12/2010 | Nobile et al. | 205/775 |

FOREIGN PATENT DOCUMENTS

| | | |
|---|---|---|
| WO | 01/15800 | 3/2001 |
| WO | 2009012112 | 1/2009 |

(Continued)

OTHER PUBLICATIONS

PCT/US2012/058559, "International Preliminary Report on Patentability", mailed Apr. 8, 2014, 6 pages.

(Continued)

*Primary Examiner* — Kyoung Lee

(57) ABSTRACT

An apparatus includes a device substrate including an array of sensors. Each sensor of the array of sensors can include a electrode structure disposed at a surface of the device substrate. The apparatus further includes a wall structure overlying the surface of the device substrate and defining an array of wells at least partially corresponding with the array of sensors. The well structure including an electrode layer and an insulative layer.

8 Claims, 19 Drawing Sheets

(52) U.S. Cl.
CPC .......... *B01J2219/00704* (2013.01); *B01J 2219/00722* (2013.01)

(56) References Cited

FOREIGN PATENT DOCUMENTS

| WO | 2010/047804 | 4/2010 |
| WO | 2012/024500 | 2/2012 |

OTHER PUBLICATIONS

"PCT/US2012/058559 International Search Report and Written Opinion mailed", Dec. 17, 2012.

Barbee, Kristopher et al., "Electric field directed assembly of high-density microbead arrays", *The Royal Society of Chemistry, Lab Chip*, vol. 9, No. 22, 2009, 3268-3274.

\* cited by examiner

ELECTRIC FIELD DIRECTED LOADING OF MICROWELL ARRAY

CROSS-REFERENCE TO RELATED APPLICATION(S)

This application is a continuation application of PCT Application No. PCT/US2012/058559, filed Oct. 3, 2012, which claims benefit of U.S. Provisional Application No. 61/542,611, filed Oct. 3, 2011, entitled "ELECTRIC FIELD DIRECTED LOADING OF MICROWELL ARRAY," and which claims benefit of U.S. Provisional Application No. 61/550,193, filed Oct. 21, 2011, entitled "ELECTRIC FIELD DIRECTED LOADING OF MICROWELL ARRAY," which are incorporated herein by reference in their entirety.

FIELD OF THE DISCLOSURE

Embodiments of the present disclosure generally relate to the field of microwell arrays. More specifically, embodiments of the present disclosure refer to loading of a microwell array with, for example, particles or microbeads using an electric field.

BACKGROUND

Electrochemical detection is attractive because it provides high sensitivity, small dimensions, low cost, fast response, and compatibility with microfabrication technologies. These characteristics led to the development of a variety of sensors based on amperometric, potentiometric, and impedimetric signals, and the assembly of sensors into an array format for chemical, biochemical, and cellular applications. Typically, in such systems, analytes are distributed among an array of confinement regions or microwells (also referred to herein as "wells" or "reaction chambers"), and reagents are delivered to such regions by a fluidics system that directs the flow of reagents through a flow cell containing the sensor array.

Some applications involve the distribution of nucleic acid molecules attached to supports (e.g., particles or microbeads) in an array format. For example, several sequencing methods involve analysis of nucleic acid libraries, where individual members of the libraries are attached to particles that are distributed into an array of microwells. For such applications, increasing the number of microwells into which particles (or microbeads) are loaded can be desirable, because empty microwells may not provide useful information. The percentage of microwells that receive a particle or microbead can be referred to as the "loading efficiency." Alternatively, in sequencing applications the loading efficiency can refer to the percentage of microwells in the array yielding a readable sequence. Poor loading efficiencies (e.g., loading efficiencies less than 50%) increase the overall cost and effort associated with a chemical/biological experiment.

Therefore, improved loading efficiencies in microwell arrays would be desirable.

SUMMARY

An apparatus includes a device substrate including sensors. A well structure overlies the surface of the device substrate and defines an array of wells at least partially corresponding with the sensors. The well structure includes an electrophoresis electrode layer and an insulative layer.

Loading particles can be performed by providing a particle suspension into a flow cell of an apparatus that includes a wall structure including an electrode layer and an insulative layer and includes a counter electrode. A voltage source electrically coupled to the electrode layer and the counter electrode can be activated to provide a voltage difference between the electrode layer and the counter electrode, whereby the particles are motivated into wells of the array of wells.

BRIEF DESCRIPTION OF THE DRAWINGS

The present disclosure may be better understood, and its numerous features and advantages made apparent to those skilled in the art by referencing the accompanying drawings.

The use of the same reference symbols in different drawings indicates similar or identical items.

DETAILED DESCRIPTION

The following detailed description refers to the accompanying drawings that illustrate exemplary embodiments consistent with this invention. Other embodiments are possible, and modifications can be made to the embodiments within the scope of the invention. Therefore, the detailed description is not meant to limit the invention.

It would be apparent to person of ordinary skill in the relevant art that the present invention, as described below, can be implemented in many different embodiments of hardware or the entities illustrated in the figures. Thus, the operational behavior of embodiments of the present invention is described with the understanding that modifications and variations of the embodiments are possible, given the level of detail presented herein.

Figure 1:
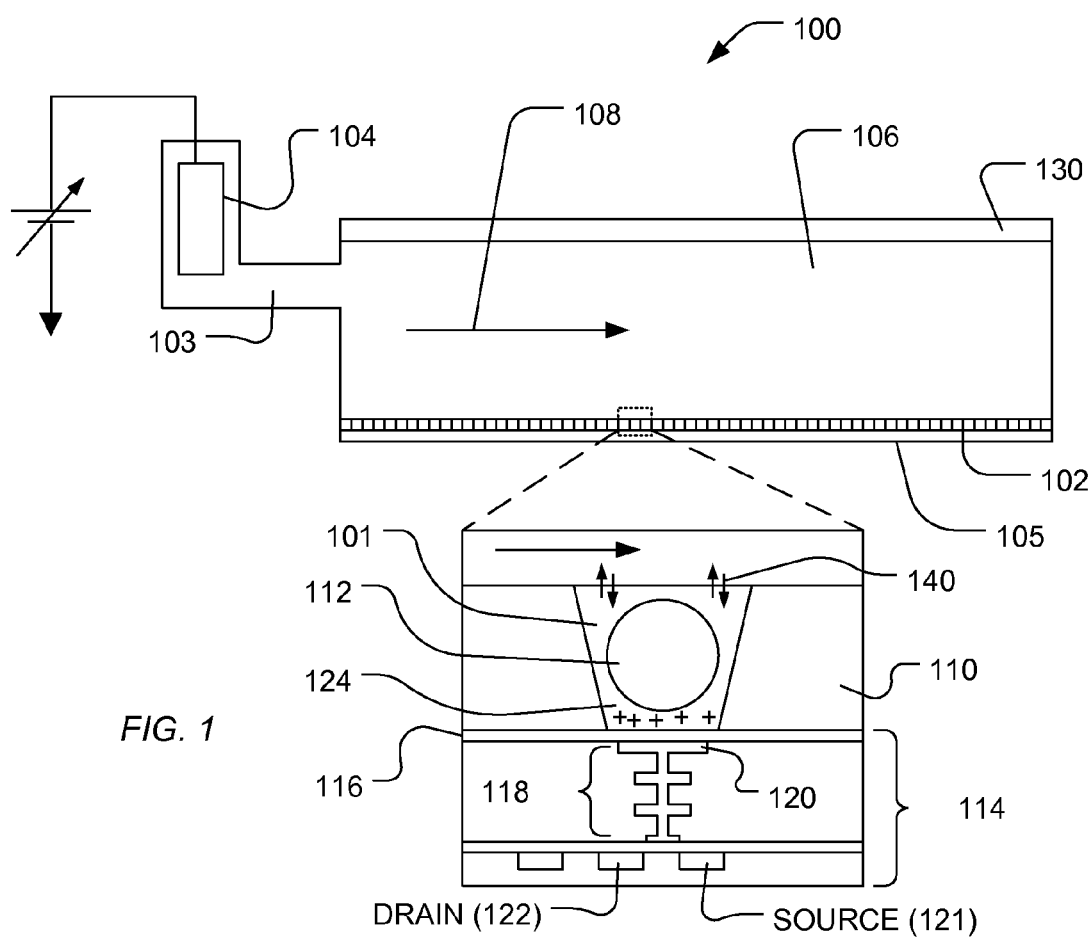
FIG. 1 is an illustration of a microwell and a sensor.

FIG. 1 is an expanded and cross-sectional view of a flow cell 100 and shows a portion of a flow cell 106. A reagent flow 108 flows across a surface of a microwell array 102, in which the reagent flow 108 flows over the open ends of the microwells. The microwell array 102 and a sensor array 105 together may form an integrated unit forming a bottom wall (or floor) of flow cell 100. A reference electrode 104 may be fluidly coupled to flow cell 106. Further, a flow cell cover 130 encapsulates flow cell 106 to contain reagent flow 108 within a confined region. Exemplary flow cell structures and associated components can be found at U.S. Patent Application Publication No. 2010/0137143 (filed May 29, 2009), which is incorporated by reference herein in its entirety.

FIG. 1 illustrates an expanded view of a microwell 101 and a sensor 114. The volume, shape, aspect ratio (such as base width-to-well depth ratio), and other dimensional characteristics of the microwells may be selected based on the nature of the reaction taking place, as well as the reagents, byproducts, or labeling techniques (if any) that are employed. The sensor 114 can be a chemical field-effect transistor (chemFET) or an ion-sensitive field effect transistor (ISFET) (together referred to as "FET") with a floating gate 118 having a sensor plate 120 optionally separated from the microwell interior by a passivation layer 116. The sensor 114 can be responsive to (and generate an output signal related to) the amount of a charge 124 present on passivation layer 116 opposite of the sensor plate 120 or on the sensor plate 120 itself. Changes in the charge 124 can cause changes in a current flowing between a source 121 and a drain 122 of the FET. In turn, the FET can be used directly to provide a current-based output signal or indirectly with additional circuitry to provide a voltage-based output signal. Reactants, wash solutions, and other reagents may move in and out of the microwells by a diffusion mechanism 140.

In an embodiment, reactions carried out in the microwell 101 can be analytical reactions to identify or determine characteristics or properties of an analyte of interest. Such reactions can generate directly or indirectly byproducts that affect the amount of charge adjacent to the sensor plate 120. If such byproducts are produced in small amounts or rapidly decay or react with other constituents, then multiple copies of the same analyte may be analyzed in the microwell 101 at the same time in order to increase the output signal ultimately generated. In an embodiment, multiple copies of an analyte may be attached to a solid phase support 112, either before or after deposition into the microwell 101. The solid phase support 112 may be microparticles, nanoparticles, beads, solid and porous comprising gels, or the like. For simplicity and ease of explanation, solid phase support 112 is also referred herein as a particle or microbead. The particle can carry a charge. In particular, polymer particles conjugated to polynucleotides can carry a charge. Alternatively, for a nucleic acid analyte, multiple, connected copies may be made by rolling circle amplification (RCA), exponential RCA, or like techniques, to produce an amplicon without the need of a solid support.

Improved loading efficiency of the microwell array 102 is desirable. The overall cost and effort associated with the microwell experiment can be improved with an increase in loading efficiency. In an embodiment, the loading efficiency of the microwell array 102 can be improved by introducing an electric field within the flow cell 106 to direct the solid phase support 112 into a microwell. The electric field directed loading of the microwell array 102 and structures to facilitate loading are described in further detail below.

As illustrated in FIG. 1, a wall structure 110 defines the well 101. The wall structure 110 can be formed of more than one layer and of more than one material. In particular, the wall structure 110 includes an electrophoresis electrode layer. A voltage, relative to a counter electrode, can be applied to the electrophoresis electrode layer to drive particles, such as the solid phase support 112, into the well 101.

Figure 2:
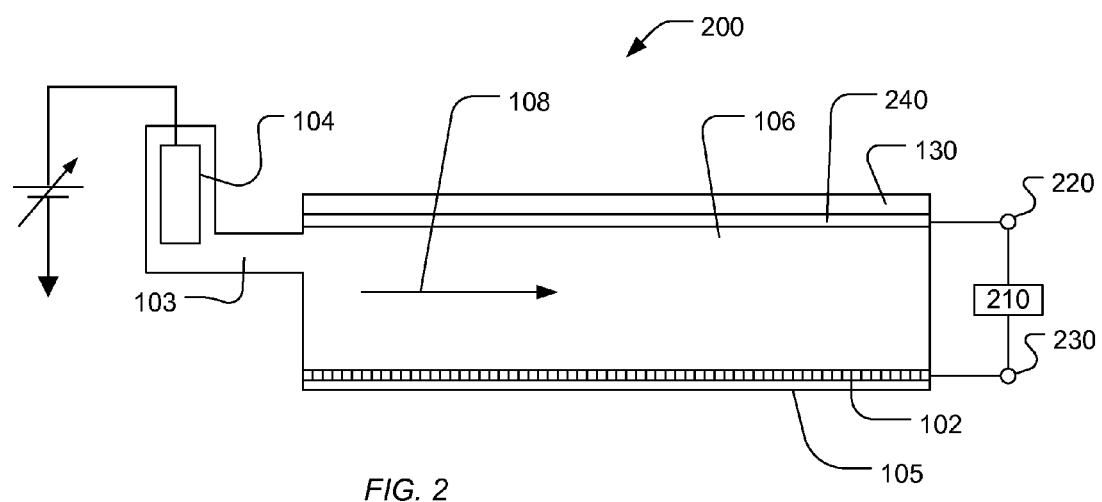
FIG. 2 is an illustration of an embodiment of a flow cell.

FIG. 2 is an illustration of a flow cell 200 according to an embodiment. The flow cell 200 includes a voltage source 210 with terminals 220 and 230. The flow cell 200 also includes a counter electrode 240 that is disposed along a surface of the flow cell cover 130. The counter electrode 240 can be, for example, an electrically conductive ceramic, such as indium tin-oxide, titanium nitride, or a combination thereof, or can be an electrically conductive polymeric material, such as conductive epoxy or other coatings. The counter electrode 240 is electrically coupled to the terminal 220, and the microwell array 102 is electrically coupled to the terminal 230, according to an embodiment. The terminal 230 is electrically coupled to the microwell array 102 via an electrophoresis electrode layer implemented in the well wall structures defining the microwells in the microwell array 102. The nature of the electrophoresis electrode in the well wall structures defining the microwells is described in further detail below.

The voltage source 210 provides an electric field to the flow cell 106 via the counter electrode 240 and the electrophoresis electrode in microwell array 102. The electric field directs a microbead (e.g., solid phase support 112 of FIG. 1) into a portion of the microwells in the microwell array 102. That is, as microbeads enter the flow cell 106 in a buffer solution to be received by the microwells in the microwell array 102, the electric field interacts with a charge on the microbeads, and the charged microbeads are directed into the wells by electrophoresis. The microbeads can be captured by the microwells through chemical, mechanical or hydrostatic techniques. In an example, an electrochemically-induced binding between a chemical property of the microwell and a chemical property of the microbead can capture the microbead in a microwell.

For instance, the microwells in the microwell array 102 can include a gold layer, and the microbeads can be coated with streptavidin. As the streptavidin-coated microbeads enter the electric field in the flow cell 106 in a buffer solution, the streptavidin-coated microbeads can be directed into the microwells by electrophoresis. Further, the streptavidin-coated microbeads can be captured by the microwells through binding between the gold and streptavidin. An example of such binding between gold and streptavidin can be found at Barbee et al., *Electric Filed Directed Assembly of High-Density Microbead Arrays*, The Royal Society of Chemistry—Lab on a Chip, Sep. 15, 2009, Issue 22, at 3268-3274, which is incorporated by reference herein in its entirety.

Figure 3:
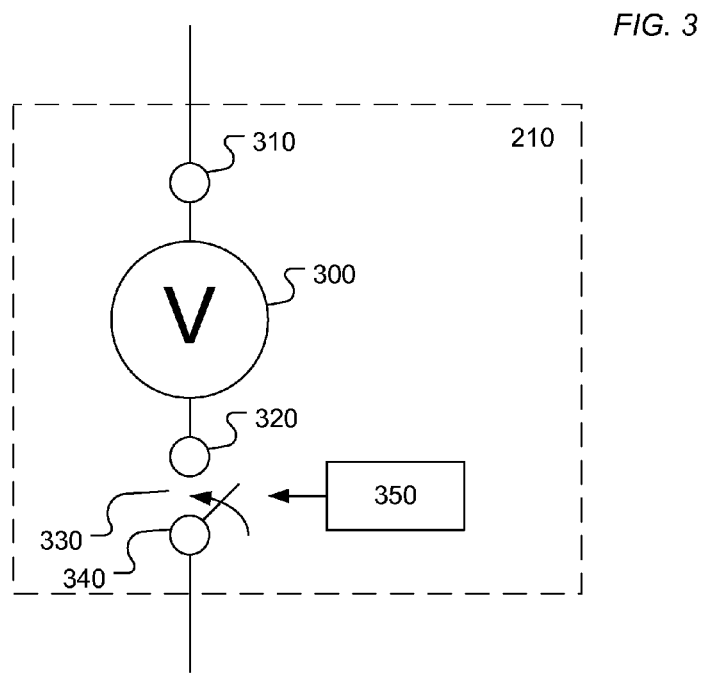
FIG. 3 is an illustration of an embodiment of a voltage source that is used in conjunction with a flow cell.

FIG. 3 is an illustration of the voltage source 210, according to an embodiment. The voltage source 210 includes a voltage supply 300 with terminals 310 and 320, a switch 330, and a pulse generator 350. The terminals 310 and 320 can be negative and positive terminals of the voltage supply 300, respectively. In an embodiment, the terminals 310 and 320 are coupled to terminals 220 and 230 of FIG. 2, respectively; in turn, the voltage potential from the terminal 310 is transferred to the counter electrode 240 of FIG. 2, and the voltage potential from the terminal 320 is transferred to the electrode in the microwell array 102 of FIG. 2 via the switch 330. The terminals 310 and 320 of FIG. 3 can be the positive or negative terminals of voltage supply 300. For ease of explanation, the terminals 310 and 320 are negative and positive terminals of the voltage supply 300, respectively, and the terminals 310 and 320 are coupled to the terminals 220 and 230 of FIG. 2, respective, for the description below.

In reference to FIG. 3, the pulse generator 350 and the switch 330 (with the voltage source 300) provide electrical pulses to the flow cell 106 of FIG. 2. In particular, based on the output of the pulse generator 350, the switch 330 opens and closes to provide a pulsed output, and thus, an electric field is generated in the flow cell 106. The pulse generator 350 can be, for example, a function generator that delivers DC voltage pulses (e.g., 3.0 V DC pulses) at a predetermined frequency and duty cycle (e.g., 1 Hz and a duty cycle of 10%). In another embodiment, a non-pulsed DC voltage can be delivered to the flow cell 106 to generate the electric field. When the switch 330 of FIG. 3 is closed, the voltage potential from the voltage source 300 is transferred to the microwell array 102 and the counter electrode 240 of FIG. 2 to generate the electric field. Alternatively, an AC voltage, such as a biased AC voltage, can be implemented in the embodiments described above.

Based on the electric field provided to the flow cell 106 of FIG. 2, the microbeads in the flow cell 106 can be directed to empty microwells by electrophoresis. Thus, as a result, the loading efficiency of the microwell array 102 of FIG. 2 is increased.

The implementation of the electrode in each of the microwells in microwell array 102 is discussed. As discussed above, the electrode associated with the microwells is electrically coupled to a voltage potential of the voltage source 300 of FIG. 3. In conjunction with the counter electrode 240 of FIG. 2, the electrode of the microwells provides an electric field in the flow cell 106 of FIG. 2.

In an exemplary embodiment, the electrodes proximal to the well wall structures and coupled to the terminal 230 are disposed at a base of the well wall proximal to the passivation layer. Alternatively, the electrode proximal to the well wall can be disposed within the well wall or on top of the well wall. In particular, the electrode can be disposed at positions between the top and the bottom of the well within the well wall and in electrical contact with fluid within the well.

Figure 4:
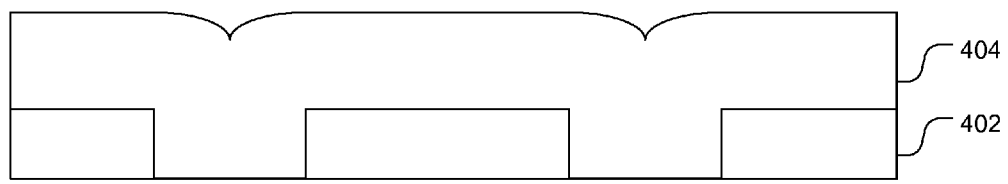
FIGS. 4-46 include illustrations of exemplary portions of exemplary sensor workpieces during stages of exemplary manufacturing processes.

In particular, the electrode can be formed while manufacturing the well wall structures that define the wells above the sensor pads. A device substrate defines an array of sensors, such as the FETs illustrated in FIG. 1. Each of the sensors of the array of sensors includes an electrode structure. The electrode structure can include a sensor pad structure exposed at the surface of the device substrate. As illustrated in FIG. 4, the pad structures 402 can be separated from each other by insulative material 404. The pad structures 402 can form a portion of a floating gate structure, such as the sensor pad 120 of the floating gate 118 illustrated in FIG. 1. In particular, the pad structures 402 can be formed of a conductive material, such as a conductive metal. The insulative material 404 can be silicon oxide, silicon nitride, silicon oxynitride, or a combination thereof.

Figure 5:
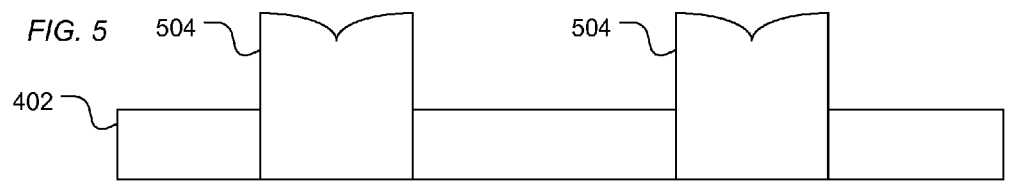

As illustrated in FIG. 5, the pad structures 402 can be exposed through the insulative material 404 to form insulation structures 504. For example, resist can be applied over the insulative material 404, a pattern can be implemented in the resist using lithography, portions of the insulating material 404 can be etched in accordance with the pattern, and any remaining resist can be stripped to expose surface of the pad structures 402. Etching can include wet etching or a plasma etching. In particular example, etching includes plasma etching with fluorinated species, such as trifluoromethane, tetrafluoromethane, nitrogen fluoride, sulfur hexafluoride, or a combination thereof.

Figure 6:
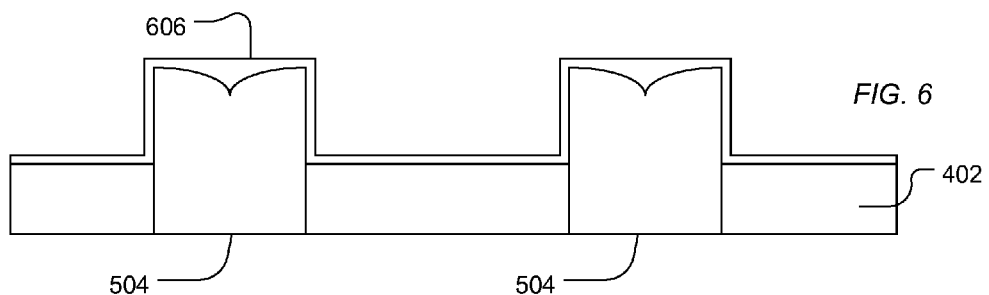

As illustrated in FIG. 6, a passivation layer 606 can be disposed over the insulation structures 504 and the pad structures 402. For example, the passivation layer 606 can be deposited using atomic layer deposition. The passivation layer 606 can also have insulative properties. In particular, layers of aluminum oxide, tantalum oxide, or combinations thereof can be deposited using atomic layer deposition. In a particular example, a three layer structure can be deposited including a first layer of aluminum oxide, a second layer of tantalum oxide, and a third layer of aluminum oxide. The passivation layer 606 can have a thickness in a range of 5 nm to 100 nm, such as 10 nm to 70 nm, such as 15 nm to 65 nm, or even 20 nm to 50 nm. Alternatively, the insulation structures 504 and the pad structures 402 can remain free of a passivation layer.

Figure 7:
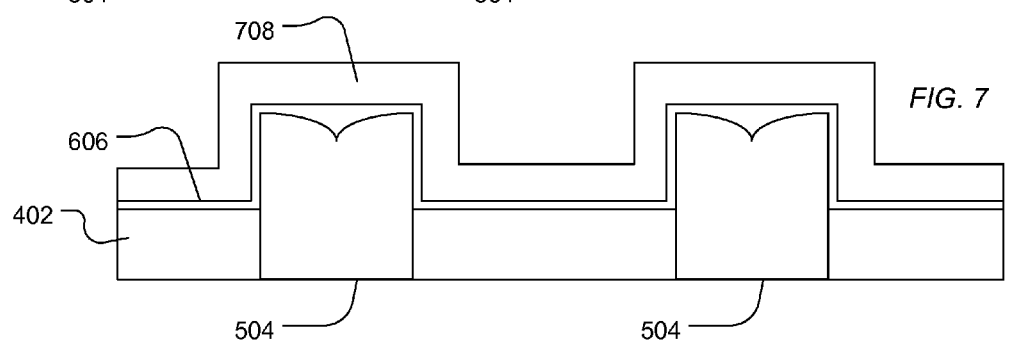

In an embodiment in which the electrode layer is deposited adjacent to the passivation layer 606, an electrode layer 708 can be deposited over the passivation layer 606, as illustrated in FIG. 7. In an example, the electrode layer 708 can be deposited using techniques such as sputtering. For example, the electrode layer can be formed of a material such as gold, silver, platinum, aluminum, copper, or a combination thereof. In an example, the electrode layer has a thickness in a range of 50 nm to 500 nm, such as a range of 80 nm to 400 nm, a range of 100 nm to 300 nm, or even a range of 100 nm to 200 nm.

Figure 8:
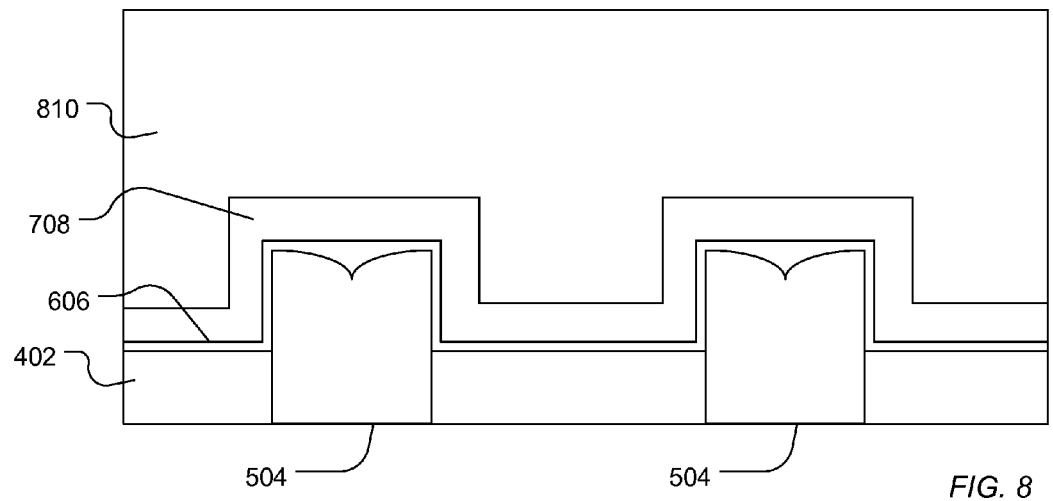

As illustrated in FIG. 8, the well wall structures can be formed of a monolithic insulative layer. For example, the layer 810 can be formed over the electrode layer 708. Alternatively, wells can be formed through a structure including more than one layer. In particular, the layer 810 can be formed of silicon dioxide, silicon nitride, silicon oxynitride, tetra orthosilicate (TEOS), other insulative materials, or a combination thereof. In particular, such materials can be deposited, for example, using chemical vapor deposition or other deposition techniques. Alternatively, the layer 810 can be formed of an insulative polymeric material, such as through spin coating or other coating techniques.

Figure 9:
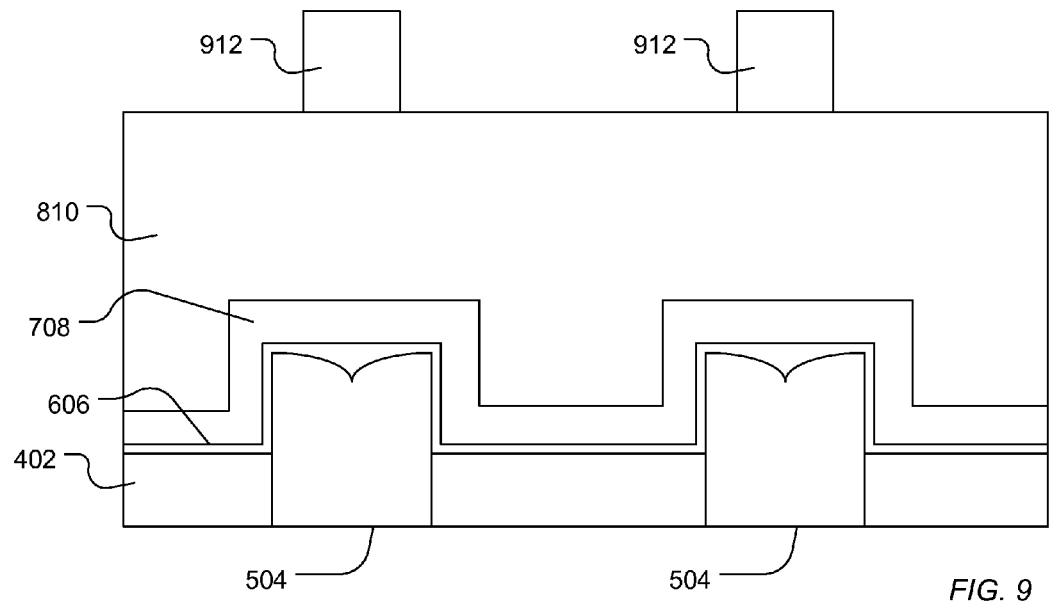

To form the well structures, openings can be formed through the layer 810 to expose the electrode layer 708 above the pad structures 402. For example, as illustrated in FIG. 9, a photoresist can be used to pattern large openings providing access to the layer 810. For example, the photoresist, using lithography, can be used to form small blocking structures 912 above the insulation structures 504.

Figure 10:
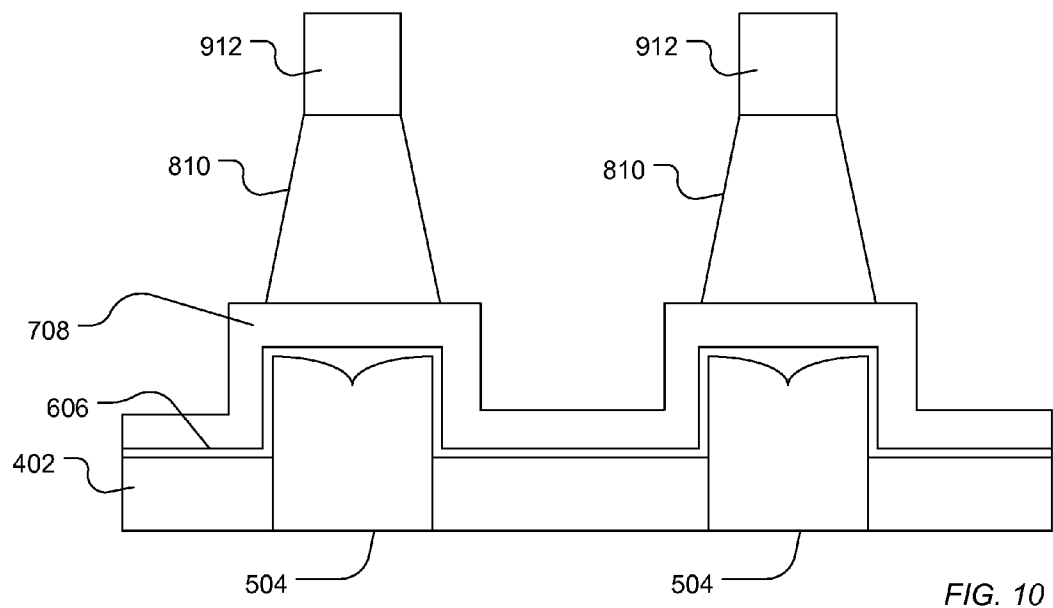
Figure 11:
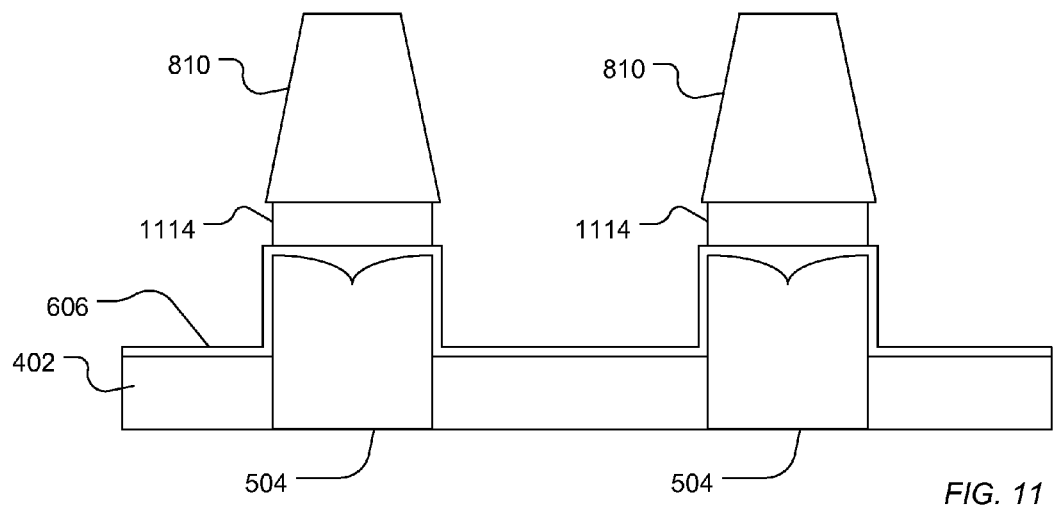

Using an etch process, the openings can be formed to expose the electrode layer 708 above the pad structures 402, as illustrated in FIG. 10. For example, a fluorinated etch with endpoint detection can be used. Such a plasma etch technique can utilize a fluorinated species, such as those described above, to form a fluorinated plasma that etches the material of the layer 810.

Following stripping of the photoresist and wet etch removal of a portion of the electrode layer 708 that extends over the pad structures 402, an electrode layer 1114 is formed underneath the well wall structure 810 and above the passivation layer 606 on top of the insulation structures 504. In particular, the electrode layer 708 can be wet etched using an acid solution including phosphoric acid, acetic acid, nitric acid, or a combination thereof to form the electrode layer 1114. As such, the electrophoresis electrode layer 1114 is exposed in wells of the array. In the case of a polymer insulative layer in place of layer 810, the polymer layer can be etch in conjunction with the electrode layer 708, bypassing one or more steps of the illustrated process.

The electrode layer 114 is physically separate from the electrode structure including the pad structure 402 and can electrically isolated from the pad structure except when a conductive fluid is present in the well. Over the pad structures 402, the passivation layer 606 is exposed. As discussed above, the electrode layer 1114 can be coupled with a terminal 230 of FIG. 2 and a charge differential can be induced between the top of a flow channel and the interior of the wells.

Figure 12:
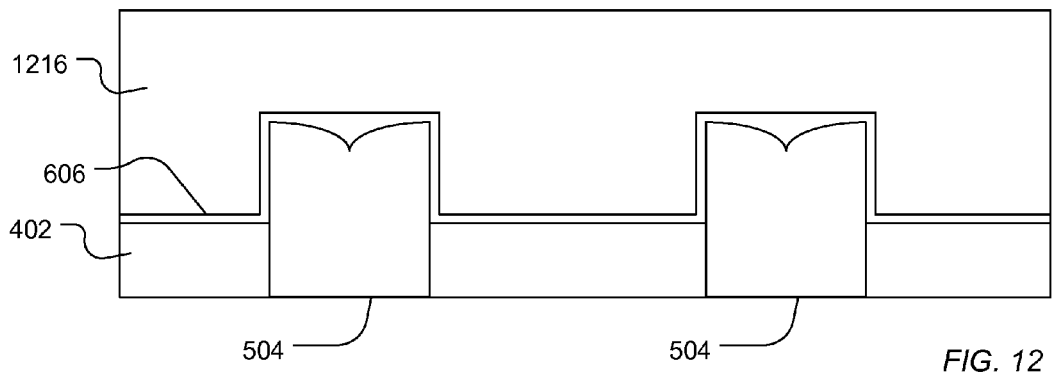

In another embodiment, the electrode can be formed within the well wall structure between the top and bottom of the well. Returning to FIG. 6, a passivation layer 606 is disposed over the pad structures 402 and the insulation structures 504. As illustrated in FIG. 12, a first insulation layer 1216 can be deposited over the passivation layer 606. For example, the insulation layer 1216 can be deposited using chemical vapor deposition and can be formed of materials, such as silicon dioxide, silicon nitride, silicon oxynitride, tetra orthosilicate (TEOS), or a combination thereof. Alternative, a polymeric insulative material can be used.

Figure 13:
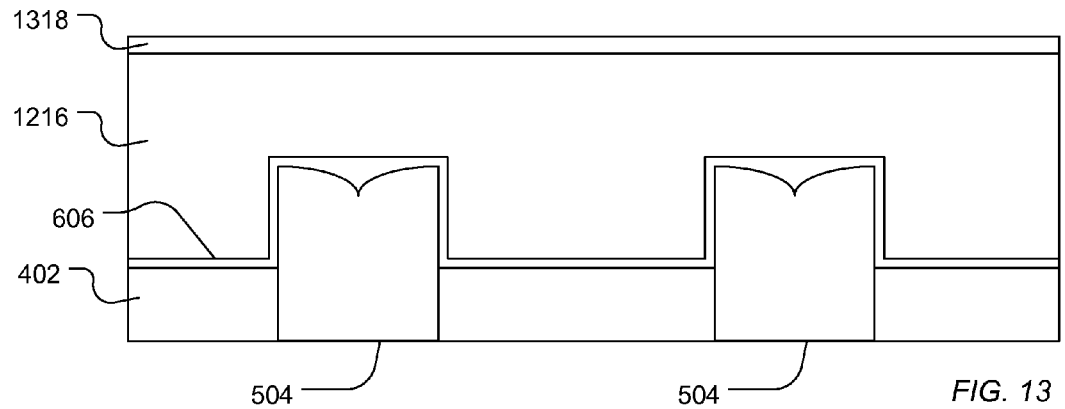

As illustrated in FIG. 13, an electrode layer 1318 can be deposited over the first insulation layer 1216. The electrode layer 1318 can be deposited using techniques, such as sputtering, and can be formed of materials such as those described above having a range of thickness as described above.

Figure 14:
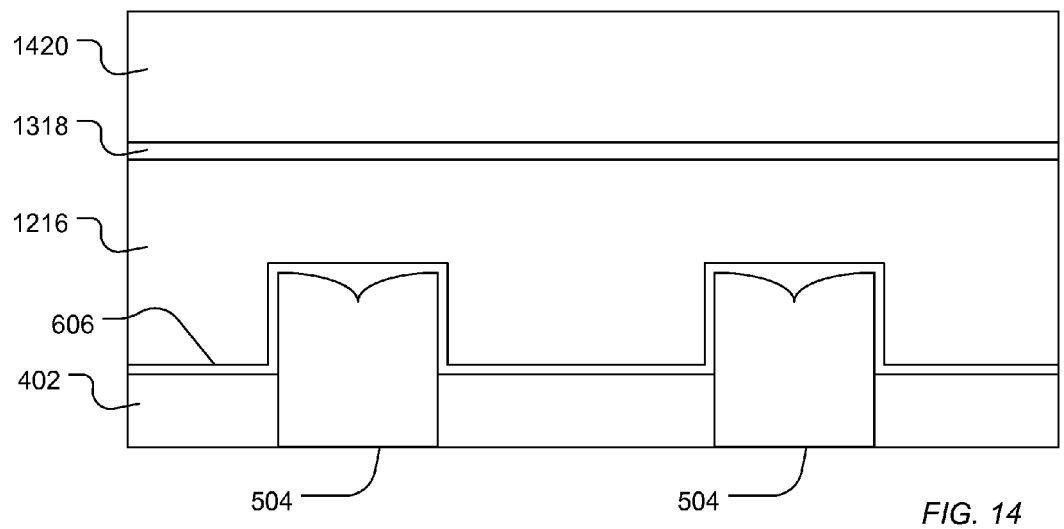

A second insulation layer 1420 can be deposited over the electrode layer 1318, as illustrated in FIG. 14. For example, the second insulating layer 1420 can be deposited using chemical vapor deposition and can be formed of a material such as silicon dioxide, silicon nitride, silicon oxynitride, tetra orthosilicate (TEOS), or combination thereof. Alternatively, a polymeric insulative material can be used.

Figure 15:
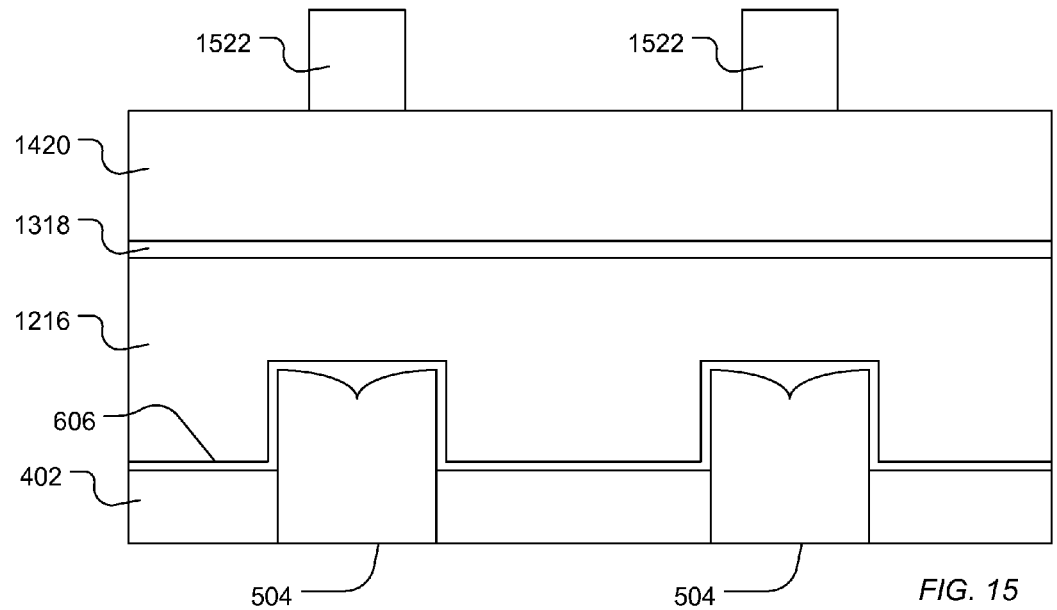

As illustrated in FIG. 15, photoresist structures 1522 can be formed, such as through lithographic techniques, above the insulation structures 504. The photoresist structures 1512 can provide a large opening for forming wells within the well wall structure.

Figure 16:
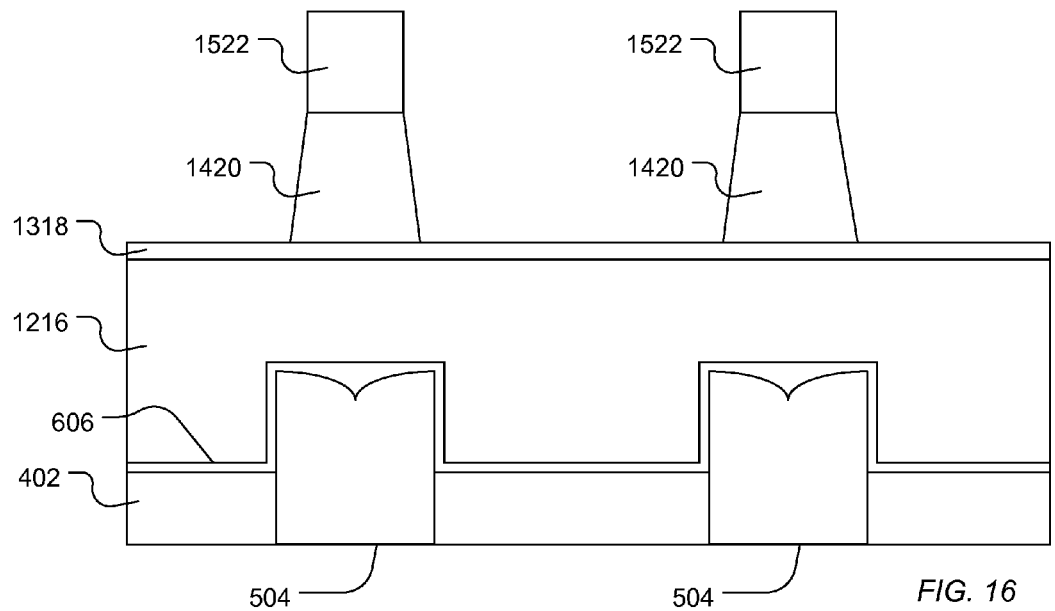

For example, as illustrated at FIG. 16, the second insulation layer 1420 can be etched to the electrode layer 1318. For example, a fluorinated etch technique with endpoint detection can be utilized. In particular, a plasma etch utilizing trifluoromethane, tetrafluoromethane, nitrogen fluoride, sulfur hexafluoride, or a combination thereof can be used to etch the second insulation layer 1420.

Figure 17:
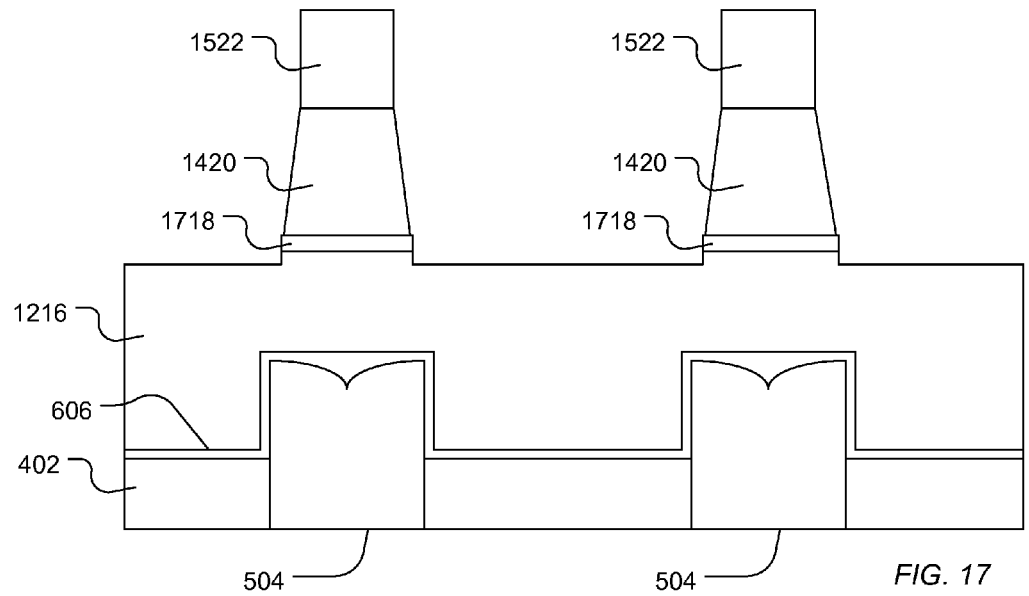

As illustrated in FIG. 17, the electrode layer 1318 can be etched to form the electrode layer 1718. In an example, the electrode layer 1318 can be wet etched. In another example, the electrode layer 1318 can be plasma etched. For example, a chlorinated etch can be used to etch through the electrode layer. In particular, some overreach may be permitted, etching beyond the electrode layer 1318 into a portion of the first insulation layer 1216.

Figure 18:
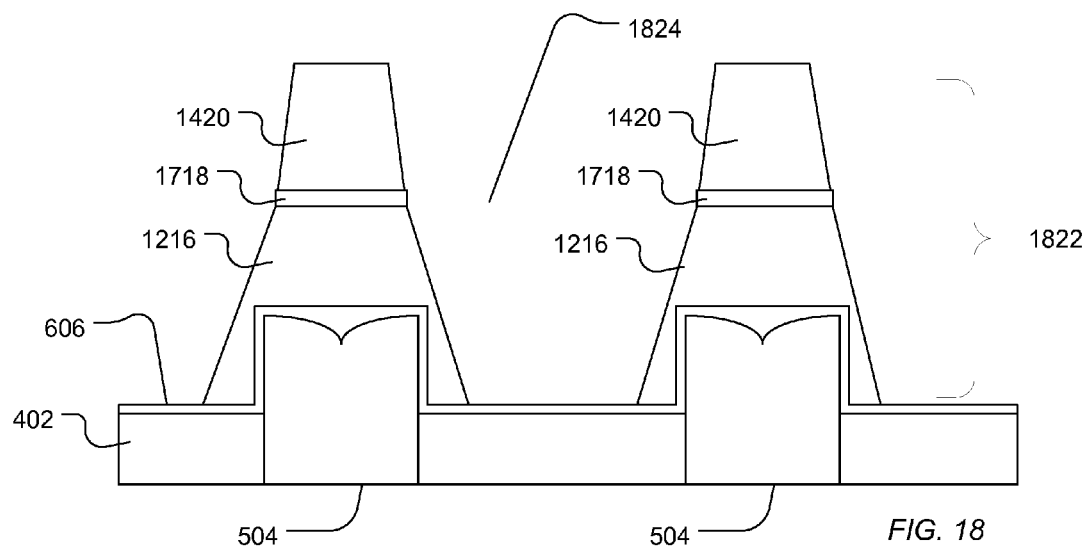

As illustrated in FIG. 18, the first insulation layer 1216 can be etched to expose the passivation layer 606 over the pad structures 402 or the pad structures 402 itself. For example, a fluorinated etch with endpoint detection can be utilized to etch the first insulating layer 1216. The resulting structure includes electrode layer 1718 disposed within the well wall structure 1822 between the top and bottom of the well 1824 and in electrical contact with fluid within the well 1824.

Figure 19:
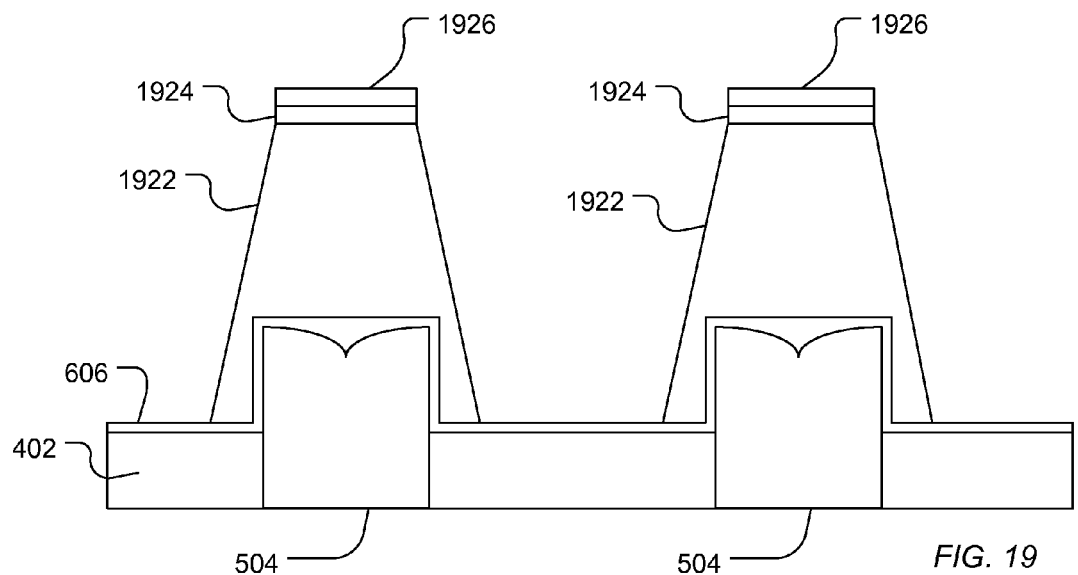

In an alternative embodiment, an electrode layer can be deposited on top of a well wall structure. For example, as illustrated in FIG. 19, an electrode 1924 can be disposed atop a well wall structure 1922. A passivation layer 606 can be positioned over the pad structures 402 and the insulation structures 504. The passivation layer 606 can be exposed through the well wall structure 1922. In each of the above embodiments, a buffer layer can be dispensed over the well wall structures. Optionally, a buffer layer or an additional insulating layer 1926 can be disposed over the electrode 1924.

Figure 20:
Figure 21:
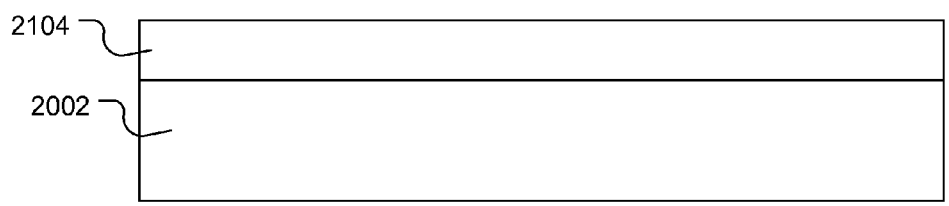

In a further exemplary embodiment illustrated in FIG. 20, a structure 2002 is provided. The structure 2002 can form the basis of a test device. In an alternative example, the structure 2002 can include an array of sensors. Each of the sensors can include a gate oxide over which a floating gate and sensor pad can be disposed. As illustrated in FIG. 21, a metal layer 2104 can be deposited over the structure 2002. In an example, the metal layer 2104 has a thickness in a range of 0.5 μm to 1.0 μm. The metal layer 2104 can be deposited using a technique described above and can include a metal selected from those identified above.

Figure 22:
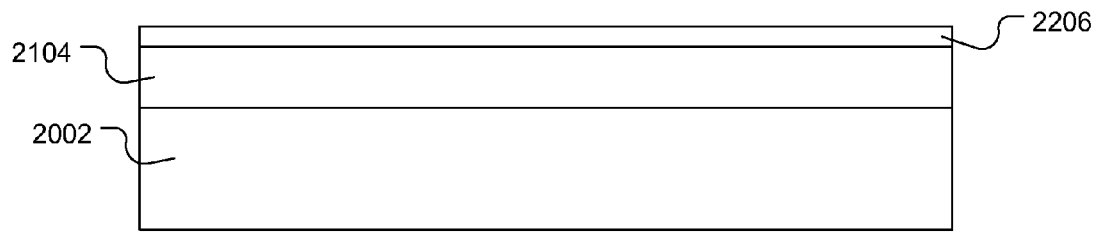

As illustrated in FIG. 22, a passivation layer 2206 can be deposited over the metal layer 2104. In a particular example, the passivation layer 2206 is deposited using atomic layer deposition. In an example, the passivation layer 2206 can include a layer of aluminum oxide having a thickness of approximately 20 nm deposited over the metal layer 2104, and can include a further layer of tantalum oxide having a thickness of approximately 40 nm deposited over the aluminum oxide.

Figure 23:
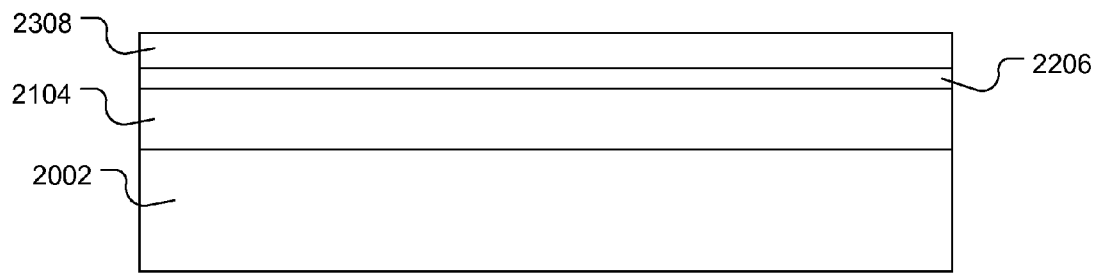

As illustrated in FIG. 23, an electrode layer 2308 can be deposited over the passivation layer 2206. In particular, the electrode layer 2308 can be formed of a conductive material, such as a metal, deposited using a method described above. In an example, the electrode layer 2308 has a thickness in a range of 0.2 μm to 0.5 μm.

Figure 24:
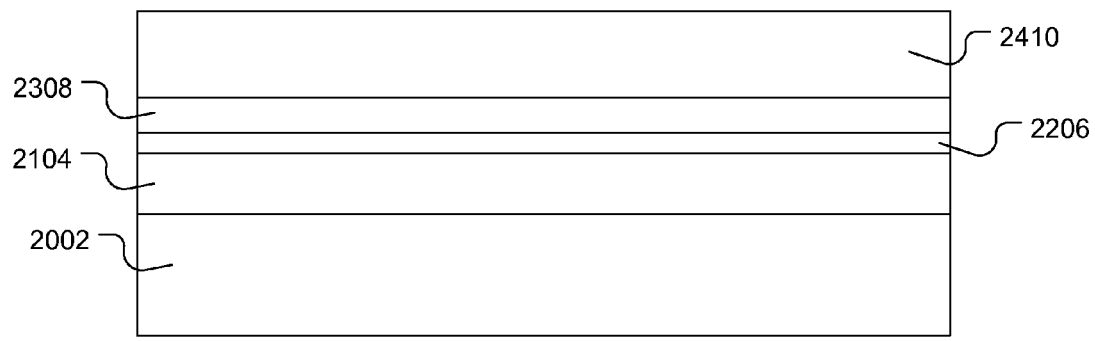

As illustrated in FIG. 24, an insulation layer 2410 can be deposited over the electrode layer 2308. In an example, the insulation layer 2410 can be formed of an oxide, nitride, or combination thereof of silicon. Alternative, a polymeric insulative material can be used.

Figure 25:
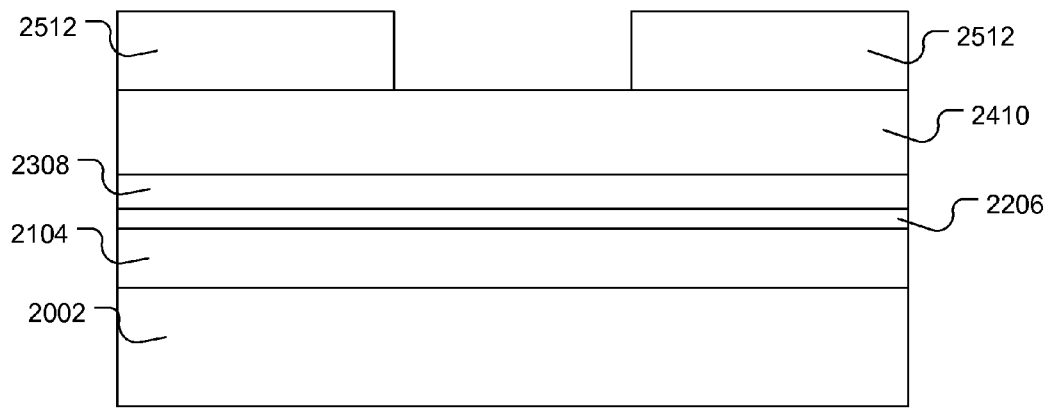
Figure 26:
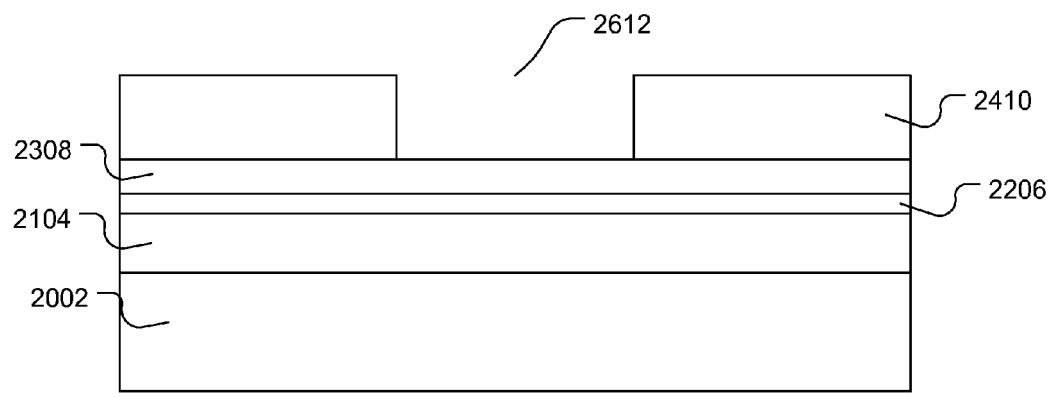
Figure 27:
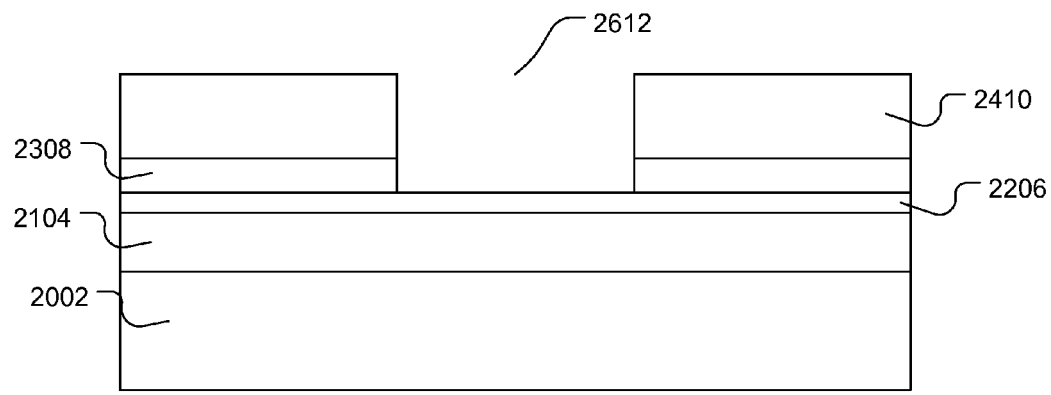

As illustrated in FIG. 25, a patterned photoresist layer 2512 can be deposited over the insulation layer 2410. The insulation layer 2410 can be etched, for example, using a fluorinated plasma etch to form a well 2612. Using a further etch process, such as a wet etch process, the electrode layer 2308 can be etched to expose the passivation layer 2206, as illustrated in FIG. 27.

Figure 28:
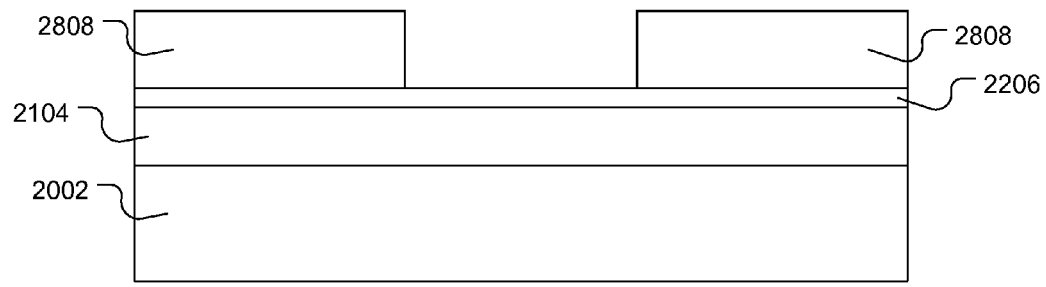
Figure 29:
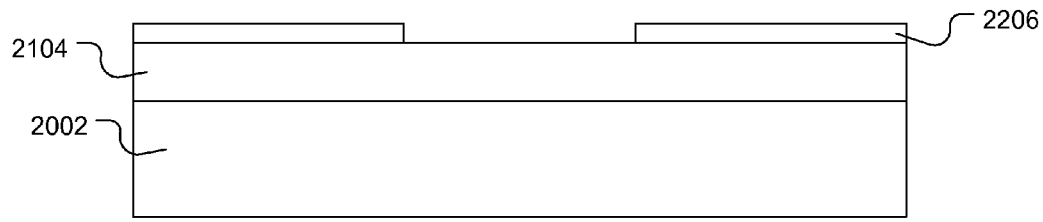
Figure 30:
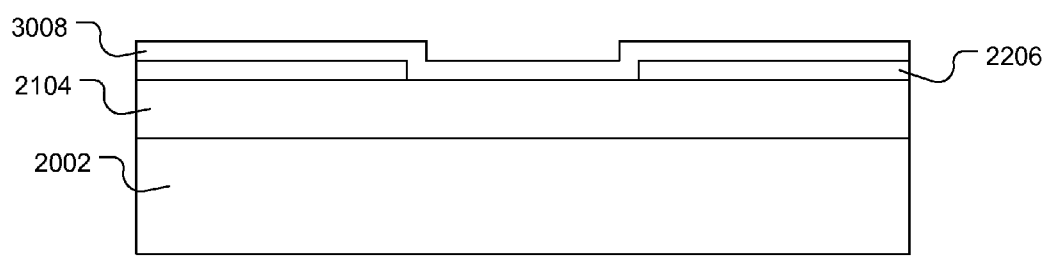

Starting with FIG. 22, a bond pad portion of the device can be formed. For example, as illustrated in FIG. 28, a patterned photoresist layer 2808 can be applied over the passivation layer 2206. As illustrated in FIG. 29, the passivation layer 2206 can be etched to expose the underlying metal layer 2104. An electrode layer 3008 can be deposited over the patterned passivation layer 2206 and the exposed metal layer 2104, as illustrated in FIG. 30. Optionally, the electrode layer 3008 can be formed in a same deposition as the layer 2308 of FIG. 23. The electrode layer 3008 and the layer 2308 can be connected. Alternatively, the electrode layer 3008 and the layer 2308 can be electrically isolated.

Figure 31:
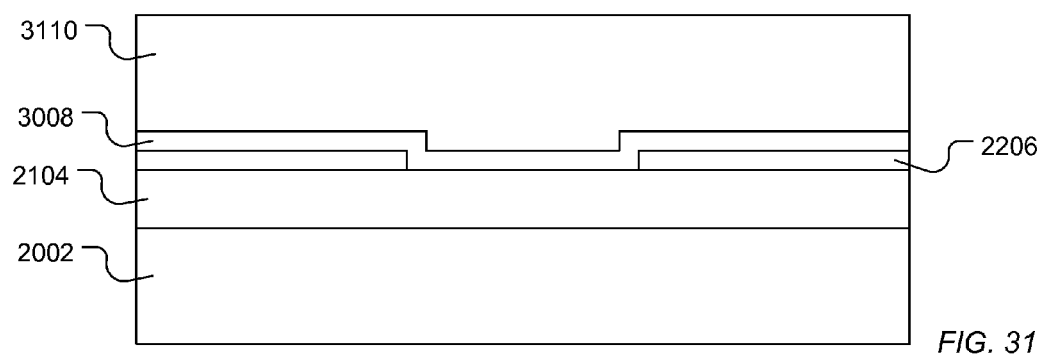
Figure 32:
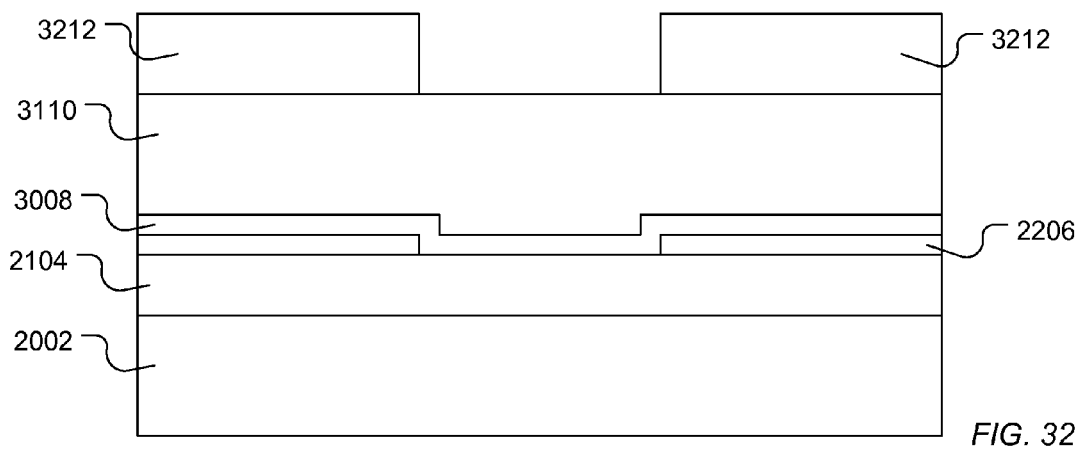
Figure 33:
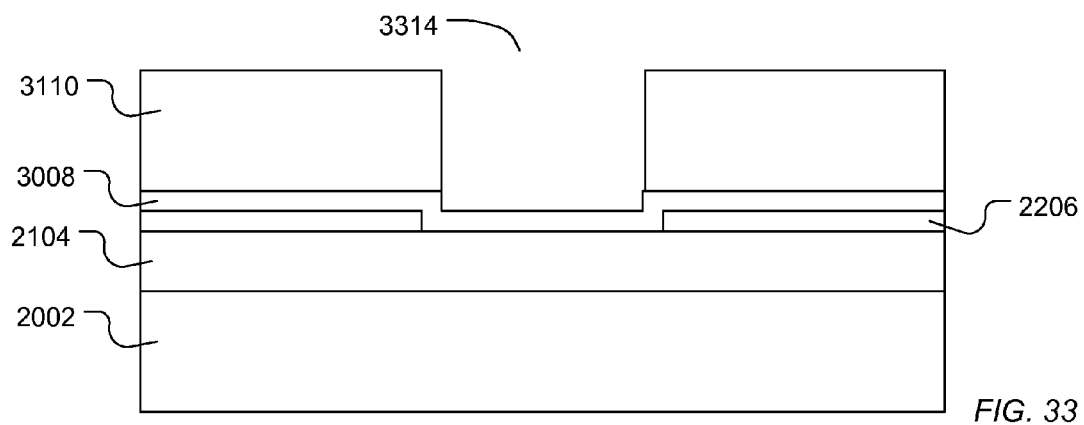

As illustrated in FIG. 31, an insulation layer 3110 can be deposited over the metal layer 3008. As illustrated in FIG. 32, a patterned photoresist layer 3212 is deposited over the insulation layer 3110. The insulation layer 3110 can be etched to expose the electrode layer 3008. An interconnect with the device can be formed by depositing a conductive material into the opening 3314.

Figure 34:
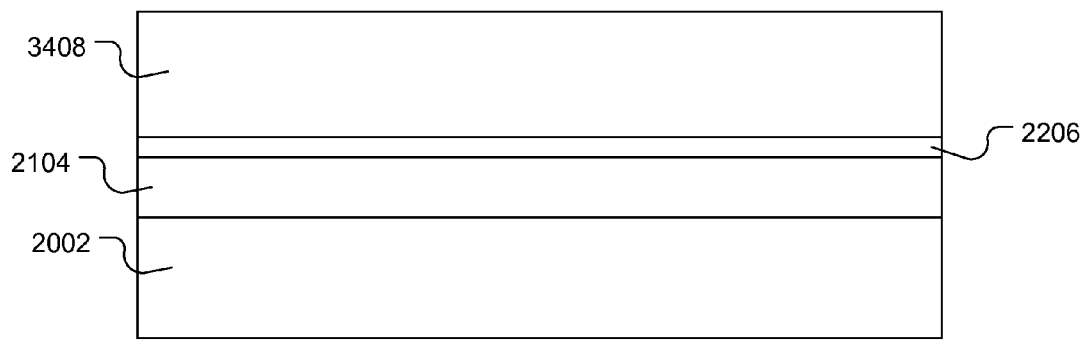
Figure 35:
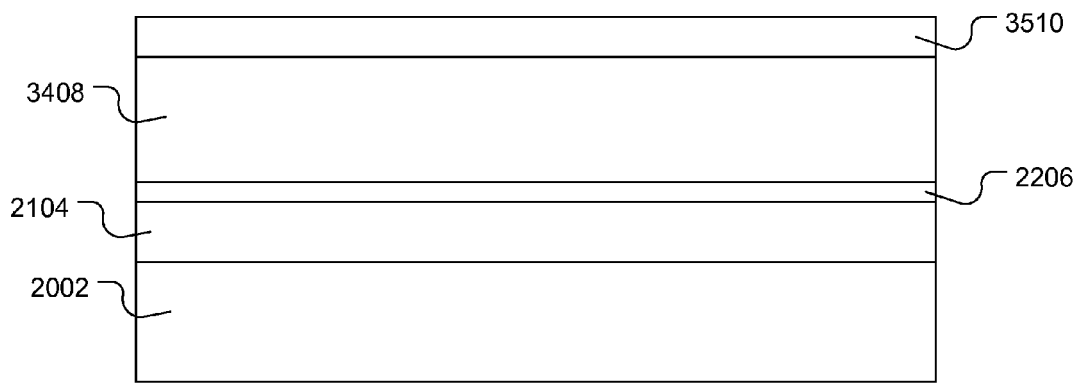
Figure 36:
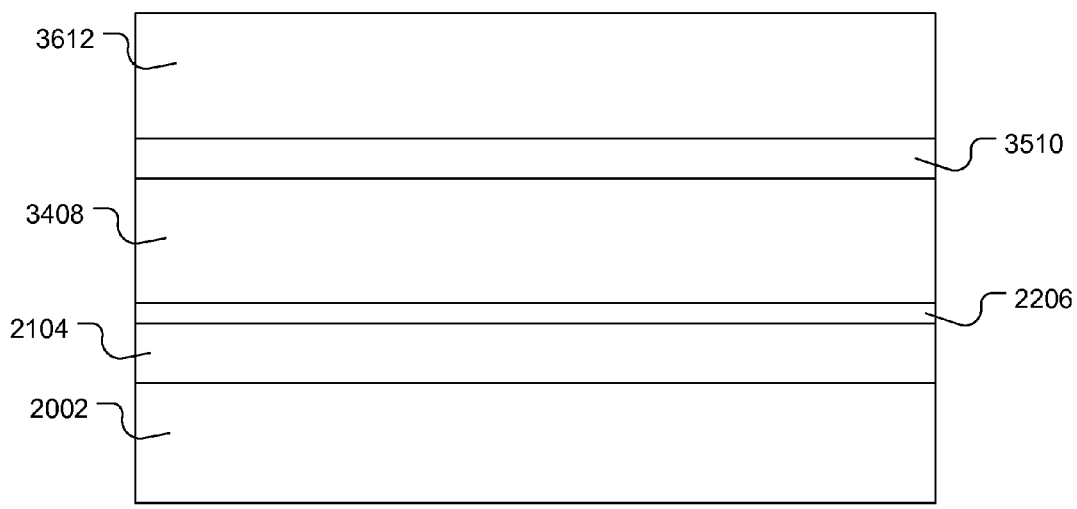

In an additional embodiment, the electrode layer can be formed within a well structure of the well wall. Starting with FIG. 22, a metal layer 2104 is deposited over a sensor structure 2002. A passivation layer 2206 is deposited over the metal layer 2104. As illustrated in FIG. 34, an insulation layer 3408 is deposited over the passivation layer 2206. An electrode layer 3510 can be deposited over the insulation layer 3408, as illustrated in FIG. 35. An additional insulation layer 3612 can be deposited over the electrode layer 3510, as illustrated in FIG. 36.

Figure 37:
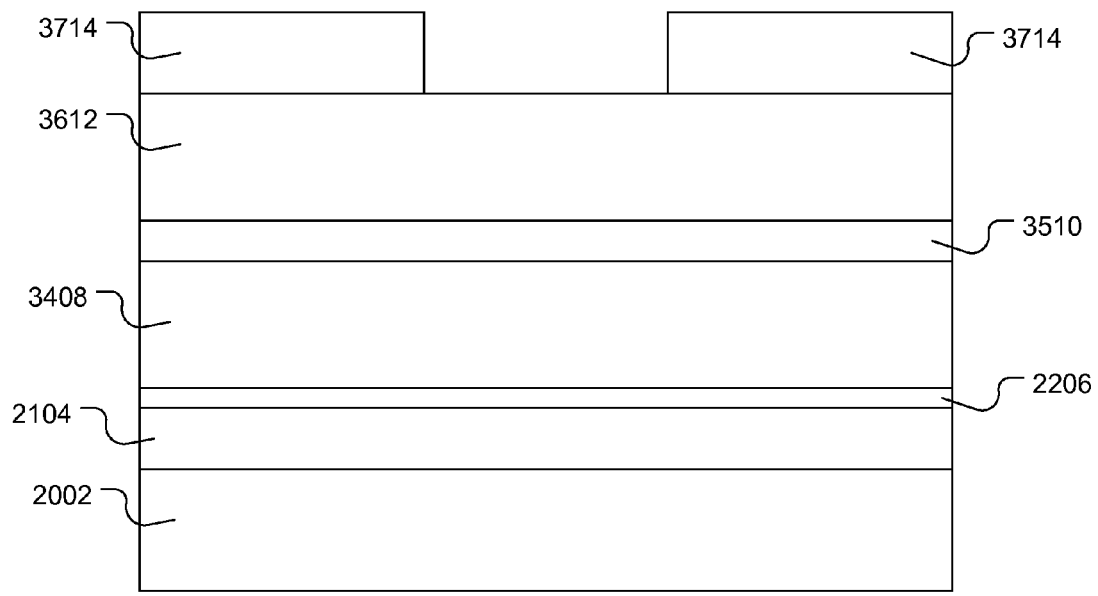
Figure 38:
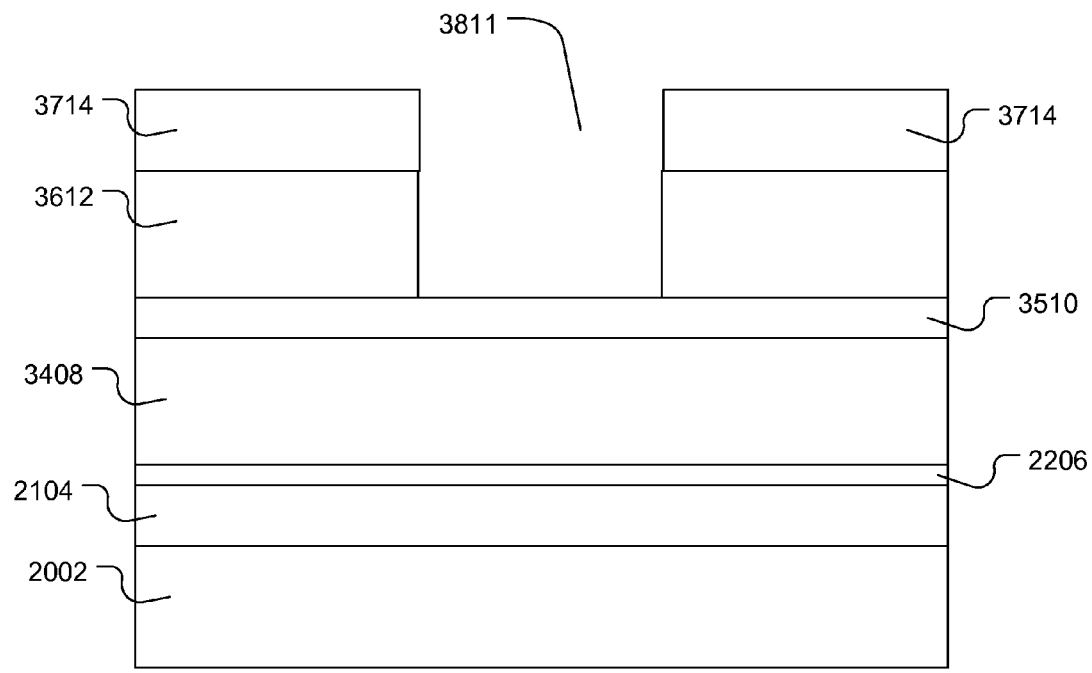
Figure 39:
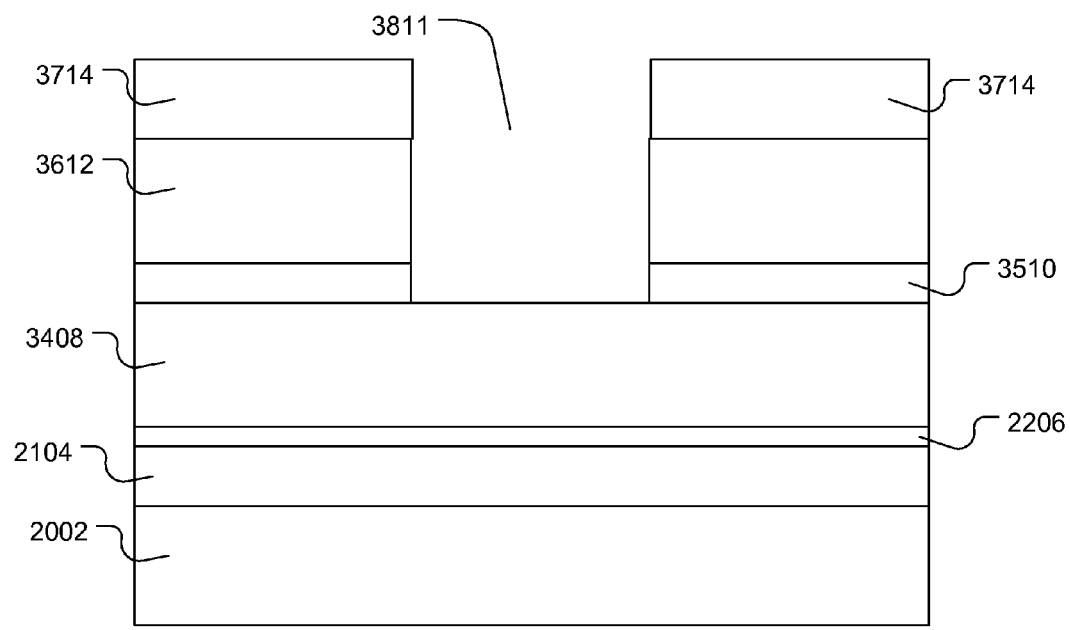
Figure 40:
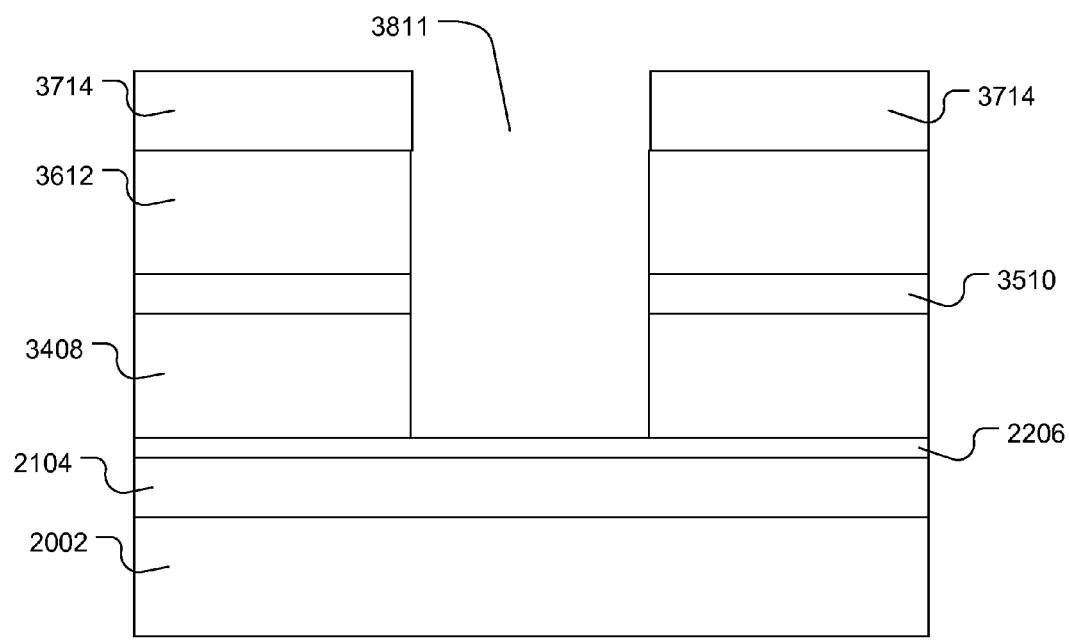

The layers can be patterned. For example, as illustrated in FIG. 37, a patterned photoresist layer 3714 can be this deposited over the insulation layer 3612, the electrode layer 3510, and the insulation layer 3408. As illustrated in FIG. 38, the insulation layer 3612 can be etched to provide an initial well 3811. For example, etching can include plasma etching, such as a fluorinated plasma etch. The electrode layer 3510 can be etched, for example, using a wet patch process, as illustrated in FIG. 39. Further, the insulation layer 3408 can be etched, for example, using a plasma etch process, such as a fluorinated plasma etch. As a result, the passivation layer 2206 disposed over the metal layer 2104 is exposed through the well 3811, as illustrated in FIG. 40.

Figure 41:
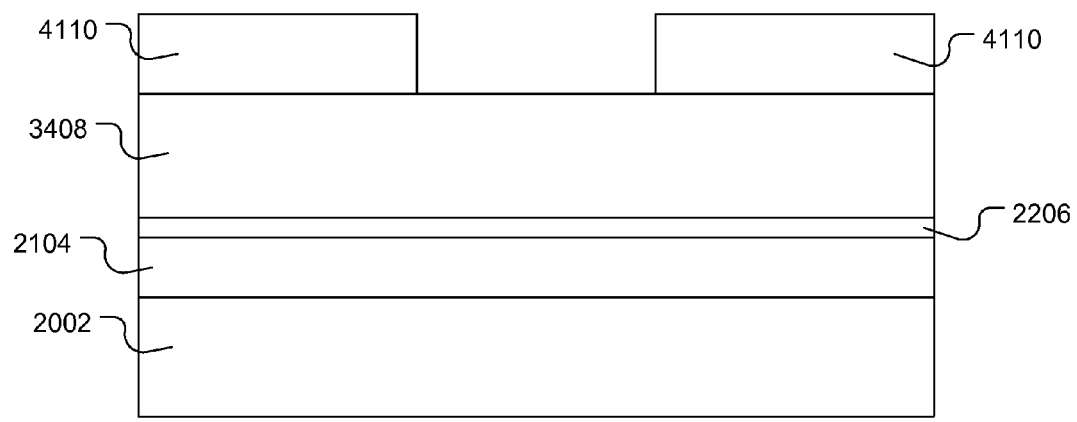
Figure 42:
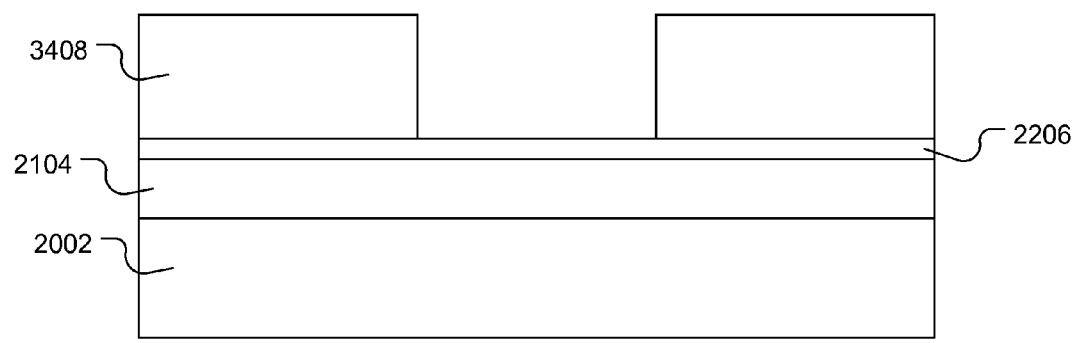

Bond pads can be formed in a different portion of the device. For example, starting with FIG. 34, a passivation layer 2206 is deposited over a metal layer 2104, and an insulation layer 2408 is deposited over the passivation layer 2206. As illustrated in FIG. 41, a patterned layer 4110 of photoresist can be applied over the insulation layer 3408. The layer 3408 can be patterned or etched in accordance with the pattern of the layer 4110. For example, as illustrated in FIG. 42, the layer 3408 can be etched using a plasma, such as a fluorinated plasma.

Figure 43:
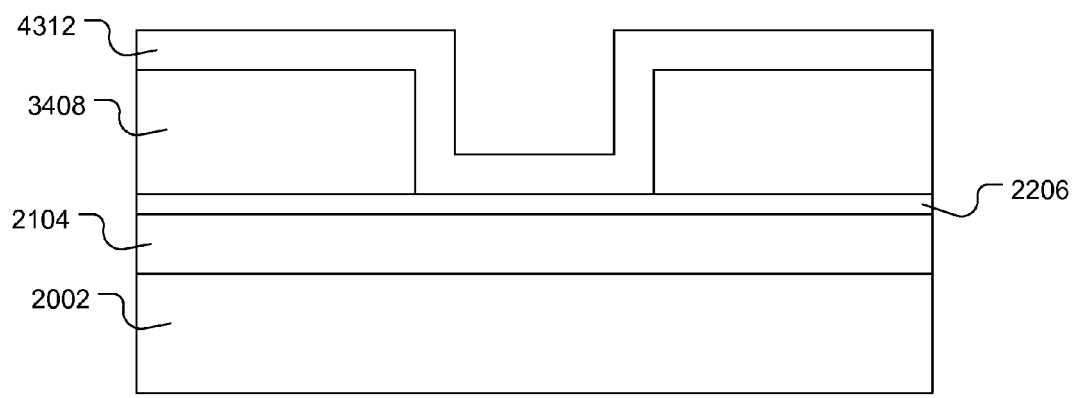
Figure 44:
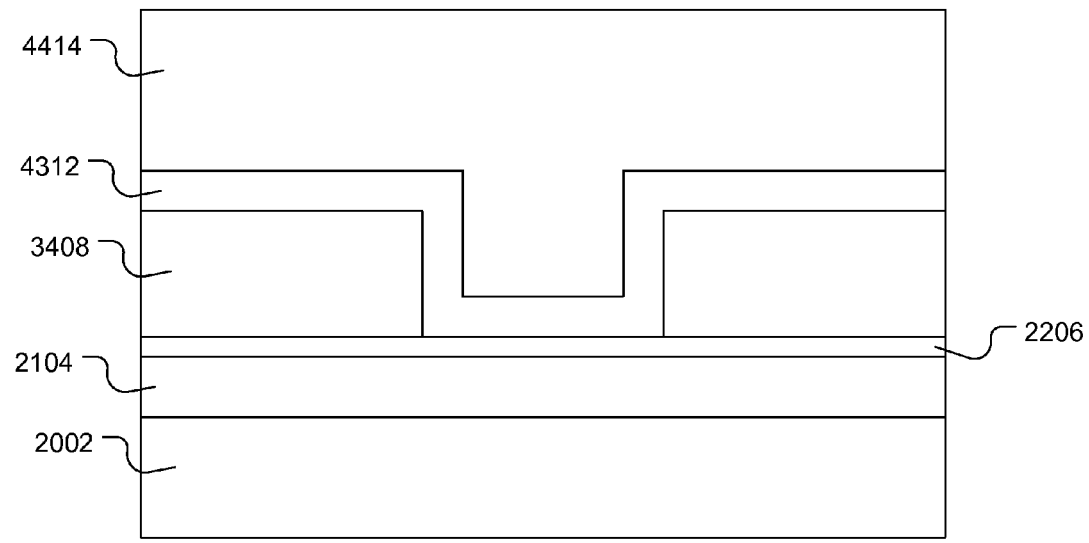
Figure 45:
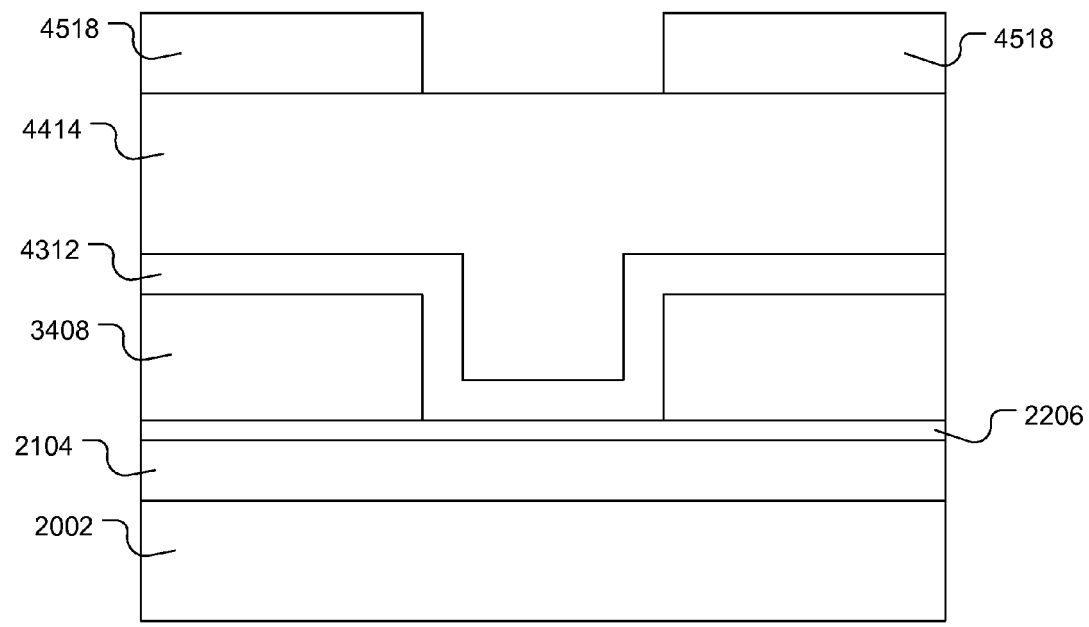

As illustrated in FIG. 43, an electrode layer 4312 is deposited over the insulation layer 3408 and passivation layer 2206. An additional insulation layer 4414 can be deposited over the electrode layer 4312. As illustrated in FIG. 45, a patterned photoresist layer 4518 can be applied over the layer 4414.

Figure 46:
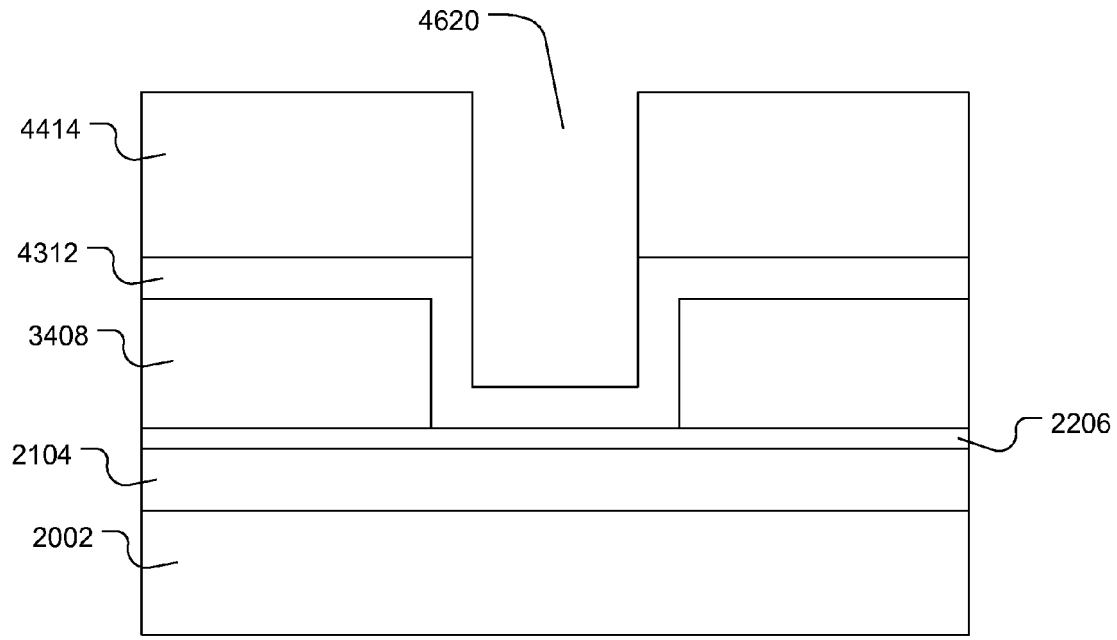

After etching, a well 4620 is formed in the layer 4414, exposing the electrode layer 4312, as illustrated in FIG. 46. A conductive material can be deposited into the well 4620 to form an interconnect.

In relation to FIGS. 20-46, techniques and materials utilized in relation to FIGS. 4-19 can be utilized. Further, while a layer, such as a metal layer may be illustrated as a single continuous layer, such a layer may be patterned and isolated from other metal layers outside of the illustrated cross-section. In addition, while not illustrated, electrical interconnects can be formed by filling voids over bond pads with conductive material. Further, while the methods for forming bond pads are provided in relation to FIGS. 20-46, similar methods can be utilized for bond pad manufacturing for those processes illustrated in FIGS. 4-19. In addition, the shape of the side walls of the illustrated wells can have a vertical orientation, an outward sloping orientation, an inward sloping orientation, or a combination thereof.

Figure 47:
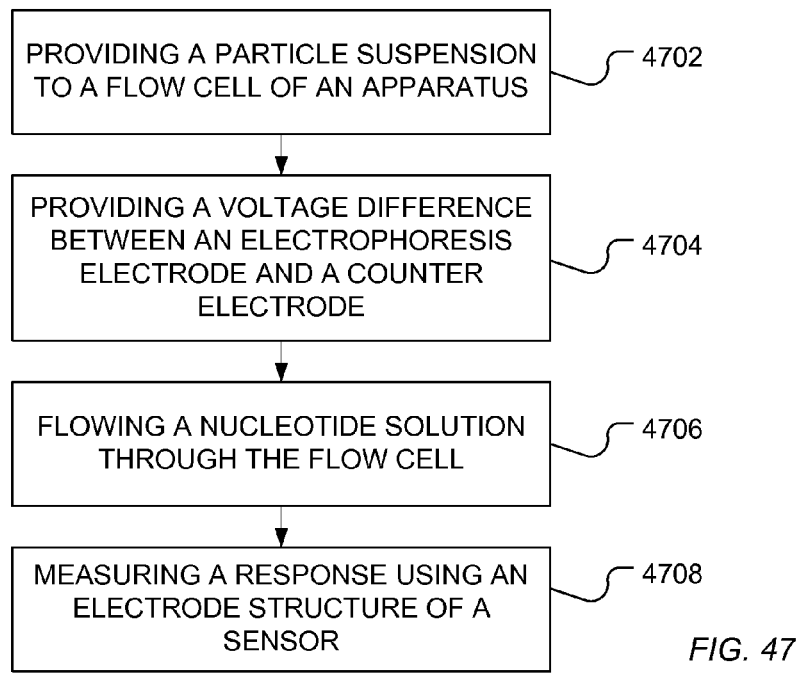
FIG. 47 includes a block flow illustration of an exemplary loading method.

The above structures can be used to load particles into wells of a device. As illustrated in FIG. 47, a particle suspension can be provided to a flow cell of an apparatus, as illustrated at 4702. For example, as illustrated in FIG. 2, a flow cell is defined above an array of wells and sensors. The particle suspension can include particles in a fluid. The fluid can be electrically conductive. Alternatively, the fluid can be non-conductive. In an example, the particles are charged particles. In a particular example, the particles are conjugated with polynucleotides.

With the particle suspension in the flow cell, a voltage difference can be applied between a counter electrode and the electrophoresis electrode, as illustrated at 4704, providing an electric field. The voltage difference can be a DC voltage difference or can be an AC voltage difference, such as a DC biased AC voltage difference. The voltage difference can be facilitated by activating a voltage source electrically connected to the counter electrode and the electrophoresis electrode.

When the apparatus is configured for use in genetic detection methods, such as sequencing, a nucleotide solution can be provided through the flow cell, as illustrated at 4706. For example, the nucleotide solution can include a single type of nucleotide in solution. In another example, the nucleotide solution can include more than one nucleotide type. A response, such as an ionic response, to the addition of the nucleotide solution can be measured by the sensors, as illustrated at 4708. For example, the sensors can be ion sensitive field effect transistors.

In a first aspect, an apparatus includes a device substrate including an array of sensors. Each sensor of the array of sensors includes an electrode structure disposed at a surface of the device substrate. The apparatus further includes a well structure overlying the surface of the device substrate and defining an array of wells at least partially corresponding with the array of sensors. The well structure includes an electrode layer and an insulative layer.

In an example of the first aspect, a well of the array of wells is to provide fluid access to a sensor of the array of sensors.

In another example of the first aspect and the above examples, a well of the array of wells exposes the electrode structure of a sensor of the array of sensors.

In a further example of the first aspect and the above examples, the electrode layer is exposed in a plurality of wells of the array of wells.

In additional example of the first aspect and the above examples, the electrode layer is electrically connected to a plurality of wells of the array of wells.

In another example of the first aspect and the above examples, the apparatus further includes an electrical interconnect separate from the array of wells providing electrical access to the electrode layer.

In a further example of the first aspect and the above examples, the insulative layer is disposed below the electrode layer and wherein a second insulative layer is disposed above the electrode layer, the array of wells defined through the insulative layer, the electrode layer, and the second insulative layer.

In an additional example of the first aspect and the above examples, a sensor of the sensor array is an ion sensitive field effect transistor.

In another example of the first aspect and the above examples, the electrode structure includes a floating electrode.

In an additional example of the first aspect and the above examples, the electrode structure is electrically isolated from the electrode layer except through fluid within the array of wells. In a further example of the first aspect and the above examples, the apparatus further includes a cover defining a flow cell over the wall structure, the flow cell to contain a fluid. In another example of the first aspect and the above examples, the apparatus further includes a counter electrode and a voltage source electrically coupled to the electrode layer and the counter electrode.

In a second aspect, a method of forming a sensor apparatus includes applying a first insulative layer over a device substrate. The device substrate includes an array of sensors. Each sensor of the array of sensors includes an electrode structure at the surface of the device substrate. The method further includes applying an electrode layer over the first insulative layer, applying a second insulative layer over the electrode layer, and forming an array of wells in the first insulative layer, the electrode layer and the second insulative layer. The array of wells substantially corresponds with the electrodes of the sensors of the array of sensors.

In an example of the second aspect, forming the array of wells includes etching the second insulative layer proximal to the electrode layer, etching the electrode layer proximal to the first insulative layer, and etching the first insulative layer to expose the electrode structure.

In another example of the second aspect and the above examples, the method further includes forming an interconnect in contact with the electrode layer.

In a further example of the second aspect and the above examples, forming the array of wells includes exposing electrode structures of the array of sensors.

In an additional example of the second aspect and the above examples, the electrode layer is electrically connected to a plurality of wells of the array of wells.

In another example of the second aspect and the above examples, a sensor of the sensor array is an ion sensitive field effect transistor.

In a further example of the second aspect and the above examples, the electrode structure includes a floating electrode.

In an additional example of the second aspect and the above examples, the electrode structure is electrically isolated from the electrode layer except through fluid within the array of wells.

In another example of the second aspect and the above examples, the method further includes applying a cover defining a flow cell over the wall structure.

In a further example of the second aspect and the above examples, the method further includes providing a counter electrode and a voltage source electrically coupled to the electrode layer and the counter electrode.

In a third aspect, a method of loading particles includes providing a particle suspension into a flow cell of an apparatus. The particle suspension includes a plurality of particles in a fluid. The apparatus includes a device substrate including an array of sensors. Each sensor of the array of sensors includes an electrode structure disposed at a surface of the device substrate. The apparatus further includes a well structure overlying the surface of the device substrate and defining an array of wells at least partially corresponding with the array of sensors. The well structure includes an electrode layer and an insulative layer. The apparatus further includes a counter electrode and a voltage source electrically coupled to the electrode layer and the counter electrode. The method further includes activating the voltage source to provide a voltage difference between the electrode layer and the counter electrode, whereby the particles are motivated into wells of the array of wells.

In an example of the third aspect, activating the voltage source includes applying a DC voltage difference between the electrode layer and the counter electrode. In another example of the third aspect and the above examples, activating the voltage source includes applying an AC voltage difference between the electrode layer and the counter electrode. In an example, the AC voltage difference is a DC biased AC voltage difference.

In a further example of the third aspect and the above examples, the plurality of particles includes nucleic acid-containing particles.

In an additional example of the third aspect and the above examples, the method further includes flowing a nucleotide solution through the flow cell and measuring an ionic response using the electrode structure.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

After reading the specification, skilled artisans will appreciate that certain features are, for clarity, described herein in the context of separate embodiments, may also be provided in combination in a single embodiment. Conversely, various features that are, for brevity, described in the context of a single embodiment, may also be provided separately or in any subcombination. Further, references to values stated in ranges include each and every value within that range.

What is claimed is:

1. A method of forming a sensor apparatus, the method comprising:
    applying a first insulative layer over a device substrate, the device substrate including an array of sensors, each sensor of the array of sensors including an electrode structure at the surface of the device substrate;
    applying an electrode layer over the first insulative layer;
    applying a second insulative layer over the electrode layer; and
    forming an array of wells in the first insulative layer, the electrode layer and the second insulative layer, the array of wells substantially corresponding with the electrodes of the sensors of the array of sensors.

2. The method of claim 1, wherein forming the array of wells comprises:
    etching the second insulative layer proximal to the electrode layer;
    etching the electrode layer proximal to the first insulative layer; and
    etching the first insulative layer to expose the electrode structure.

3. The method of claim 1, further comprising forming an interconnect in contact with the electrode layer.

4. The method of claim 1, wherein forming the array of wells includes exposing electrode structures of the array of sensors.

5. The method of claim 1, wherein the electrode layer is electrically connected to a plurality of wells of the array of wells.

6. The method of claim 1, wherein a sensor of the sensor array is an ion sensitive field effect transistor.

7. The method of claim 1, wherein the electrode structure includes a floating electrode.

8. The method of claim 1, wherein the electrode structure is electrically isolated from the electrode layer except through fluid within the array of wells.

* * * * *